United States Patent [19]

Grage, Jr. et al.

[11] Patent Number: 5,488,816
[45] Date of Patent: Feb. 6, 1996

[54] METHOD AND APPARATUS FOR MANUFACTURING A COAGULATION ASSAY DEVICE IN A CONTINUOUS MANNER

[75] Inventors: Henry M. Grage, Jr., Carmel; Stanley G. Brown, Jr., Indianapolis; Michael W. Alderink, Westfield; Elon T. Van Buren; Waring C. Lynch, both of Indianapolis, all of Ind.

[73] Assignee: Boehringer Mannheim Corporation, Indianapolis, Ind.

[21] Appl. No.: 278,424

[22] Filed: Jul. 21, 1994

[51] Int. Cl.$^6$ ............... B65B 3/04; B65B 9/04; B65B 29/00
[52] U.S. Cl. ............... 53/471; 53/281; 53/437; 53/474; 53/553; 141/280
[58] Field of Search ............... 53/474, 471, 475, 53/437, 454, 453, 428, 560, 525, 553, 281, 235; 141/280, 368, 363, 89

[56] References Cited

U.S. PATENT DOCUMENTS

| | | | |
|---|---|---|---|
| 2,513,852 | 7/1950 | Donofrio | 53/454 |
| 4,437,294 | 3/1984 | Romagnoli | 53/553 |
| 4,849,380 | 7/1989 | Sawhill | 501/20 |
| 4,921,021 | 5/1990 | Andersson | 53/559 X |
| 5,016,425 | 5/1991 | Weick | 53/471 X |
| 5,110,727 | 5/1992 | Oberhardt | 435/13 |
| 5,315,810 | 5/1994 | Eaton | 53/437 X |

*Primary Examiner*—James F. Coan
*Attorney, Agent, or Firm*—Felfe & Lynch

[57] ABSTRACT

A ribbon-like flat web having a plurality of side by side depressions is fed through a horizontal slot having a downward facing surface having an aperture communicating with a reservoir of reagent containing solution. The web is urged against the downward facing surface to provide sealing as the solution is fed into the upward facing depressions. The aperture communicating with the reservoir is profiled as a parallelogram having a leading edge which is oblique to the direction of movement. After emerging from the dispensing apparatus the exposed solution is dried in hot air, followed by spray application of a second solution, further drying in hot air, and application of a backing to form capillary chambers. The method is especially useful for manufacturing coagulation assays having magnetic particles and thromboplastin.

17 Claims, 4 Drawing Sheets

METHOD AND APPARATUS FOR MANUFACTURING A COAGULATION ASSAY DEVICE IN A CONTINUOUS MANNER

BACKGROUND OF THE INVENTION

The invention relates to a method for manufacturing a coagulation assay device by a continuous process, and to an apparatus for dispensing a reagent containing solution into a plurality of side by side depressions in a ribbon-like flat web.

U.S. Pat. No. 4,849,380 discloses a device for performing an assay by using capillary action to draw a predetermined volume of a liquid sample into a reaction chamber charged with a reagent, where the reaction between the liquid sample and the reagent is monitored. The device includes a base, a spacer having an aperture therethrough laminated against the base, and a cover having a pair of apertures therethrough laminated against the cover to form a chamber having an application port and a vent. After treatment to make the chamber hydrophillic, reagent supplied to the application port by pipette is drawn into the chamber by capillary action and then freeze dried or air dried at room temperature. The thickness of the spacer is critical in order to assure capillary action, and to assure that the chamber has a predetermined volume so that the reagent therein has a predetermined concentration.

The device of U.S. Pat. No. 4,849,380 is especially suitable for a coagulation assay wherein the reaction chamber contains a coagulation reagent such as thromboplastin and inert magnetic particles such as magnetite suspended in the reagent. When a sample of blood or plasma is introduced into the chamber, the dry reagent is solubilized, the magnetic particles settle, and a coagulation reaction is initiated. When an alternating magnetic field is applied, the orientation of magnetic particles changes synchronously with the field; this effect can be monitored optically by changes in intensity of reflected light (flickering). Peak to peak values of light intensity fall off when a clot has started to form, providing a convenient assay for coagulation. Refinements in the method for monitoring the clotting time are disclosed in U.S. Pat. No. 5,110,727 and PCT International Publication No. WO 92/01065.

The processes used to manufacture the known assay device are batch processes which require wetting the reaction chamber with detergent, blowing it out, applying an aqueous reagent solution to the application hole with a pipette, then lyophilizing, i.e., rapid freezing followed by dehydration in the frozen state under high vacuum. This is especially time consuming and not convenient to high throughput manufacturing. However, the possibility of a continuous strip process has not been suggested due to the problem of drying reagent solution in the reaction chambers. Further, magnetic particles must be uniformly dispersed in the reaction chamber to facilitate optical monitoring of the fluctuations between bright and dim reflected light. This is rendered difficult by the tendency of the magnetic particles to settle out prior to application, and further by their tendency to flow toward the vent hole when resuspended by the sample as it is introduced to the chamber. This tendency also mitigates against applying the magnetic particles and the thromboplastin in a two step process.

U.S. Ser. No. 08/114,579, filed Aug. 31, 1993 and incorporated herein by reference, discloses an improved carrier solution for the magnetic particles. This solution lends itself especially to air drying and is resoluble as readily as freeze dried materials. At the same time, the aforementioned tendency of the magnetic particles to aggregate in the sample is avoided. However an efficient method of applying the particle containing solution to the assay devices in a continuous process is not disclosed.

SUMMARY OF THE INVENTION

The present invention relates to a process for manufacturing a coagulation assay device in continuous web form by feeding a two part laminate having side by side depressions through a dispensing station where a first solution containing magnetic particles fills the depressions, then passing the open depressions through a first drying station where the first solution is dried with hot air. Following this a second reagent solution containing thromboplastin is selectively sprayed in the depressions so as to be confined to a desired reaction area, then the open depressions are passed through a second drying station.

According to a preferred method, the application hole and the vent hole are punched through the laminate at opposite ends of each depression after the drying steps. Finally, a transparent cover in web form is laminated over the two part laminate having first and second dried reagents in the side by side depressions, and the assembly is severed between each pair of reaction chambers so formed to complete the individual assay devices.

The process according to the invention employs a specially designed apparatus for dispensing the first solution into the side by side depressions in the two part laminate. This device includes a base having a downward facing surface, a reservoir mounted above the base, and a pad of resilient material which loads the laminate against the downward facing surface. An aperture between the reservoir and the downward facing surface dispenses the first solution into the upward facing depressions as the laminate is moved past the aperture, the resilient pad providing sealing. An aperture shaped as a parallelogram having two sides parallel to the direction of movement and two sides at 80 degrees to the direction of movement has been found to be especially effective. The pad is preferably mounted on a rigid plate mounted parallel to the downward facing surface at an adjustable distance. Agitation means such as a high speed blade-type mixer is provided in the reservoir to assure uniform dispersion of magnetic particles.

The invention offers the advantage of high production rates not possible in the batch process of the prior art.

A further advantage is the uniform dispersion of magnetic particles in the reaction chamber.

An important advantage is the ability to achieve localized concentrations of the thromboplastin in the reaction chamber without affecting the uniform dispersion of the magnetic particles. Thromboplastin can be localized in a better area for timing the reaction.

DETAILED DESCRIPTION OF THE PREFERRED EMBODIMENT

Figure 1:
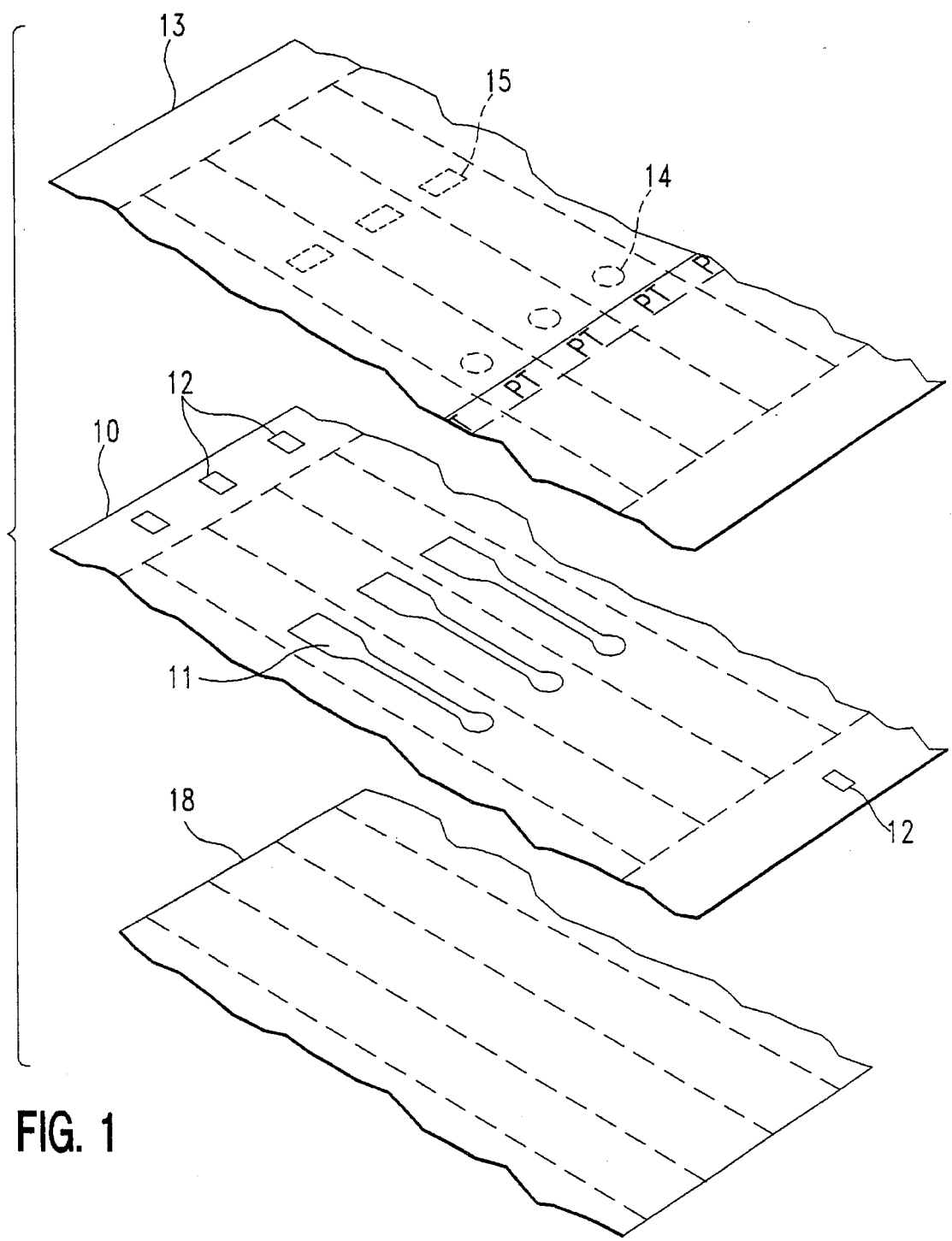
FIG. 1 is a perspective of the webs for the cover, spacer, and backing.

FIG. 1 is a perspective of the components used to manufacture the assay device according to the method of the present invention. The ribbon-like spacer 10 is a five-part laminate including a translucent central layer of MELINEX, a trademark of ICI for a biaxially stable polyester films, layers of adhesive on opposed surfaces, and protective liners over the adhesive layers (the protective layers are removed during manufacture). Such a five layer composite is available from Adhesive Research, Inc. Keyhole shaped apertures 11 are punched five at a time through the spacer 10, simultaneously with indexing holes 12 along the margins. One of the protective liners (not shown) is then removed and the spacer 10 is adhered to transparent cover 13, which is printed with indicia of origin on the same surface which is adhered to the spacer 10. Prior to joining the spacer 10 to cover 13, the cover is subjected to a corona treatment to improve the hydrophillic properties of the cover surface exposed through the apertures. Finally, the laminated web is wound on a spool for use in the process of FIG. 2. One of the protective liners remains in place, and the backing 18 is not yet part of the laminated web.

Figure 2:
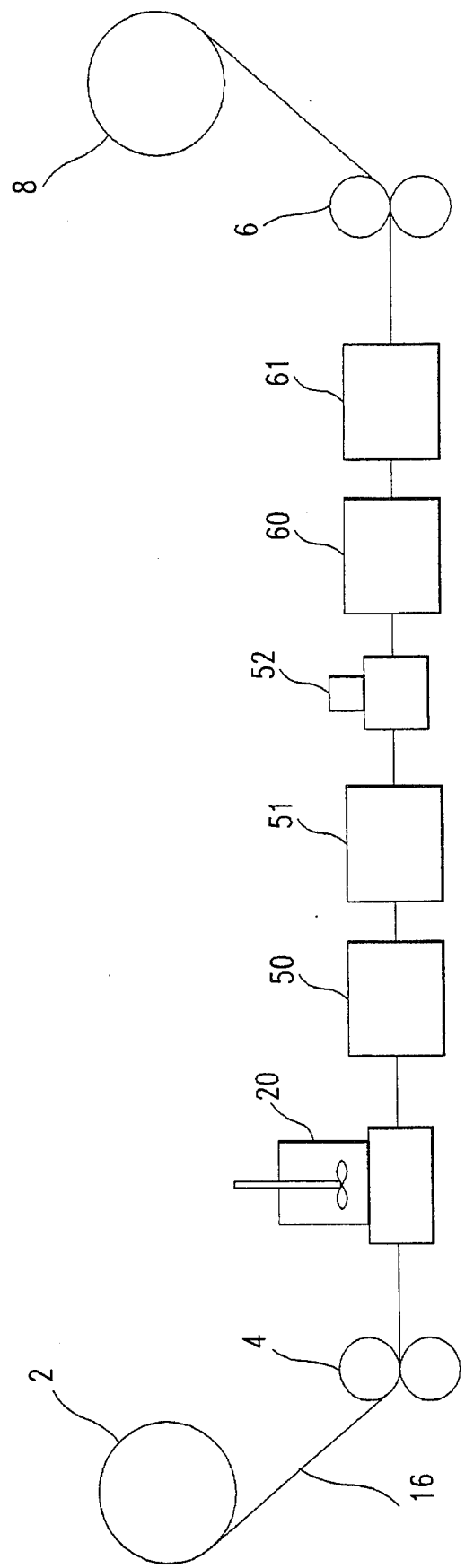
FIG. 2 is a schematic of the manufacturing apparatus.

Referring to FIG. 2, the spool 2 holds the laminated web 16 formed by joining the spacer 10 and cover 13. This web is fed between pinch rollers 4 to a dispensing apparatus 20 where a first solution containing magnetite particles is dispensed into upward facing depressions formed by apertures 11, thence to driers 50 and 51 where the solution is evaporated by hot air as the web 16 moves continuously therethrough. At dispenser 52 a second solution containing thromboplastin is sprayed continuously into the wide end of the keyhole shaped depressions. The spraying unit is a simple atomizer which is fed with the solution under pressured and compressed air. The second solution is then dried at hot air driers 60 and 61, and the semifinished laminate is drawn through pinch rollers 6 and wound onto spool 8. The temperature range in the four driers 50,51 and 60,61 is in the range of 50° to 65° C. at 200 cfm airflow and a strip speed of 1.7 m/min. Note that the liner between depressions is also exposed to second solution and dried, but this is subsequently removed.

When the spool 8 of FIG. 2 is full, it is removed to another line where the web 16 is unwound for punching the application holes 14 and vents 15 shown in phantom in FIG. 1. Following this, (1) the remaining liner on the exposed surface of the spacer 10 is removed, and (2) the transparent backing 18 (FIG. 1) is applied to the exposed adhesive to enclose the depressions 17, thereby forming the reaction chambers of the finished assay devices. The dimensions of the strips are then optically measured, and those which fail are marked for disposal. The marginal portions containing the indexing holes 12 are trimmed off, and the finished web is then sheared along parallel lines between the reaction chambers to form the finished assay devices, the rectangular vents 15 being used for optical indexing for this final shearing step.

Figure 3:
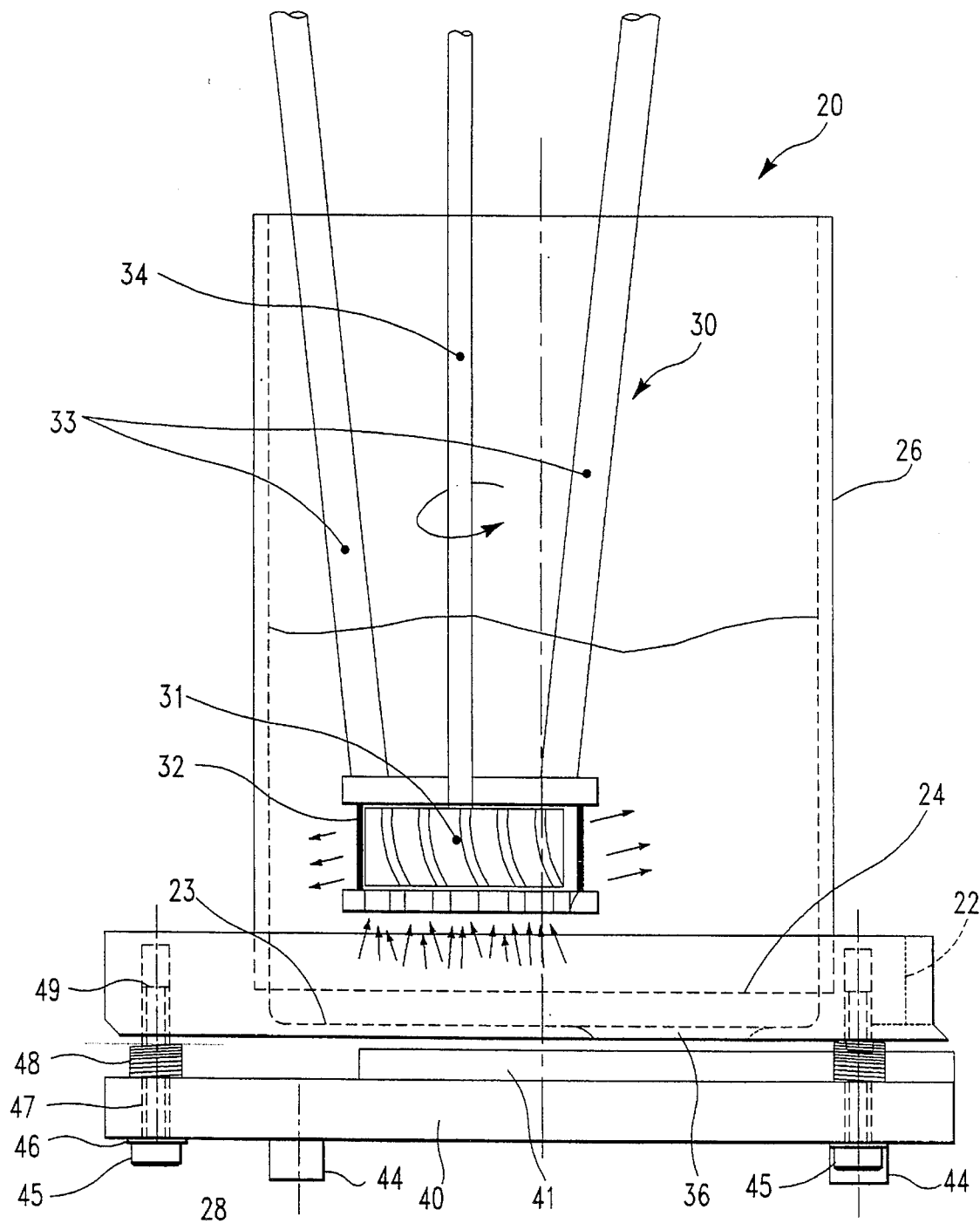
FIG. 3 is a side elevation view of the reagent dispensing apparatus with strip passing therethrough.
Figure 4:
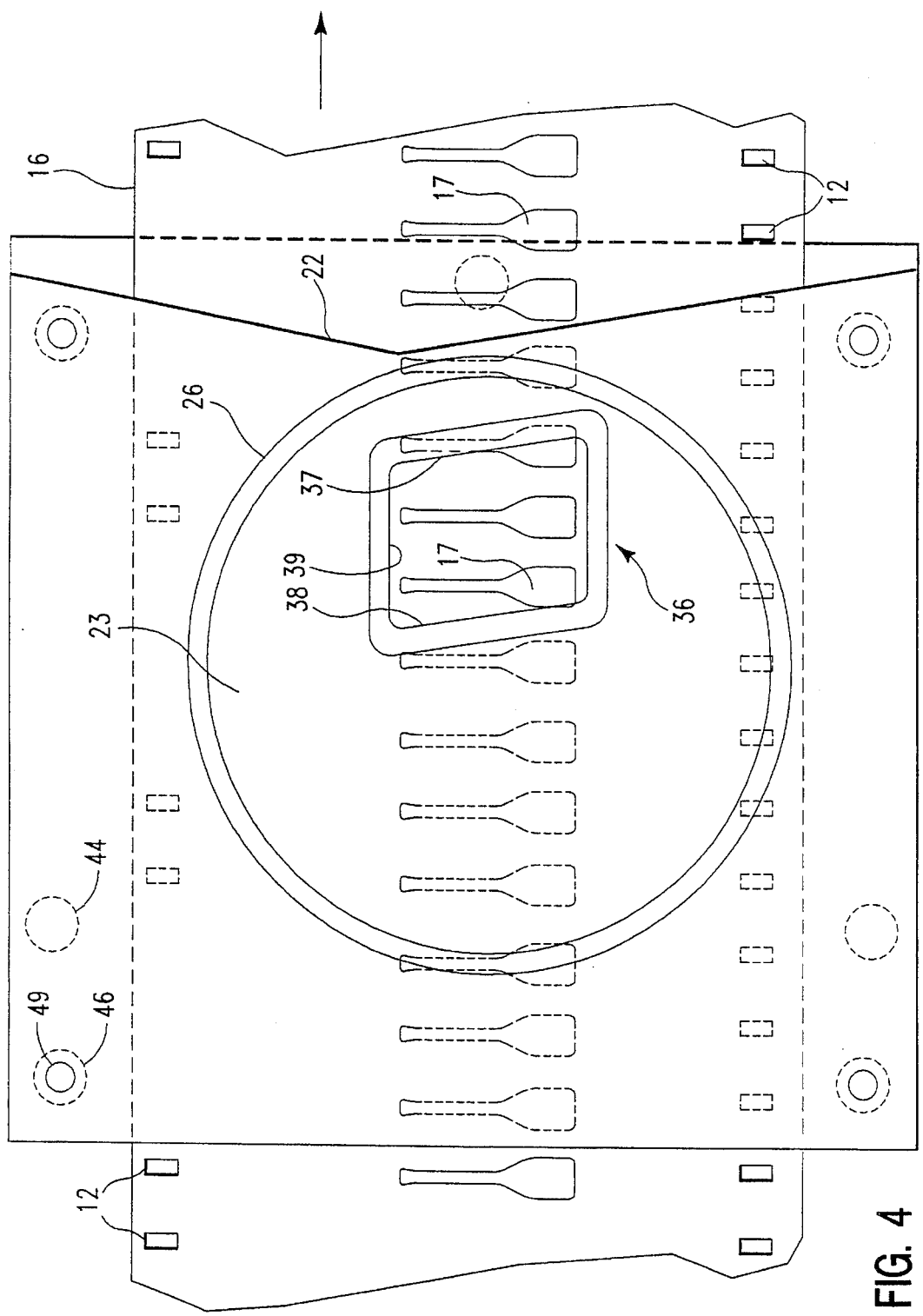
FIG. 4 is a plan view of the dispensing apparatus.

FIGS. 3 and 4 show the reagent dispensing apparatus 20 in greater detail. The base 22 is preferably made of anodized aluminum, which is machined to form an inset surface 23, and a counter sunk annular sealing surface 24 which receives tube 26 thereagainst to form a reservoir. The base 22 is grounded when the apparatus is in use. A drag plate 40 is held parallel to a downward facing surface 28 of the base by four screws 45 and associated washers 46. The screw shanks are received through unthreaded bores 47 in the drag plate and threaded bores 49 in the base. Coil springs 48 concentric to the screw shanks load the drag plate away from the base 21, and a resilient pad 41 fixed to the drag plate loads the web 16 toward the downward facing surface 28. This provides a sealing action as the first reagent containing solution is dispensed through aperture 36 into upward facing depressions 17 in the web 16. The pad 41 is preferably foam rubber with a Teflon coated surface to reduce friction. The assembly is supported by studs 44 on the drag plate 40, but adjustable mountings and/or fixed screw mountings are also possible.

The mixer 30 includes mixing blades 31, a surrounding screen 32, support struts 33, and a drive shaft 34. This assures that magnetite particles are uniformly dispersed in the solution even when a low viscosity solvent is used.

Referring especially to FIG. 4, the aperture 36 is preferably configured as a parallelogram which converges from the inset surface 23 toward the downward facing surface 28, where the web 16 is exposed with keyhole shaped troughs 17 facing upward. The leading edge 37 and trailing edge 38 of the aperture 36 extend obliquely to the direction of movement of the web 36, while the side edges 39 are parallel to the movement. Disposing the edges 37, 38 at eighty degrees to the direction of movement assures a smooth transition of the depressions 17 from the reservoir, thus preventing turbulence which could cause the magnetite particles to settle in a non-uniform array in the depressions. It also avoids catching the edge of depression 17 in a damaging way. Likewise, the provision of a trailing edge 22 on the base 21 at an oblique angle to the direction of movement assists in achieving a smooth and non-turbulent emergence of the depressions from the sealing area. The upward facing liner surface on the web is silicone coated to minimize drag as web passes through the dispensing device and to provide a hydrophobic surface. This encourages the reagent to remain only in the depressions. The pooled first reagent containing solution thus enters the drier 50 in a homogenous state, and the solvent is evaporated with the iron containing particles uniformly dispersed in a readily resolubilizable carbohydrate matrix.

The foregoing is exemplary and not intended to limit the scope of the claims which follow.

We claim:

1. Process for manufacturing an assay device, comprising the following steps:

feeding a ribbon-like flat web having a plurality of upward facing side-by-side depressions in a direction of movement through a horizontal slot having a downward facing surface, dispensing a first reagent-containing solution into said depressions through an aperture between said downward facing surface and a reservoir containing said first solution, and drying said first solution with air while said strip is in said horizontal plane, after said strip emerges from said slot.

2. Process as in claim 1 further comprising agitating said first solution in said reservoir, whereby a suspended reagent is uniformly distributed in said first solution.

3. Process as in claim 1 further comprising loading said strip against said downward facing surface, thereby providing a sealing action around said aperture.

4. Process as in claim 1 further comprising adhering a ribbon-like flat backing to said strip over said depressions, thereby forming a ribbon-like assembly having a plurality of capillary spaces containing dried reagent, providing a pair of spaced apart holes communicating with each capillary space, and severing said assembly between said capillary spaces to form a plurality of assay devices.

5. Process as in claim 4 wherein said pair of spaced apart holes are provided by forming said holes through said strip in each depression after drying said first solution but before adhering said backing.

6. Process as in claim 1 further comprising dispensing a second reagent containing solution into said depressions after said first solution is dried, and drying said second solution with air.

7. Process as in claim 6 wherein said second solution is dispensed by spraying.

8. Process as in claim 6 wherein said air for drying said second solution has a temperature of 50°–65° C.

9. Process as in claim 1 wherein a ribbon-like cover and a ribbon-like spacer having a plurality of side-by-side apertures therethrough are adhered together to form said ribbon-like flat strip.

10. Process as in claim 1 wherein said air for drying said first solution has a temperature of 50°–65° C.

11. Apparatus for dispensing a reagent containing solution into a plurality of side-by-side depressions in a ribbon-like flat strip, comprising a base having a downward facing surface, a means for loading a ribbon-like web against said downward facing surface, thereby providing a sealing action around said aperture, a reservoir holding a first reagent containing solution over said base, and an aperture between said reservoir and said downward facing surface, whereby said solution may be dispensed into upward facing depressions in said web as said web is moved past said aperture in a direction of travel.

12. Apparatus as in claim 11 wherein said means for loading said ribbon-like web against said downward facing surface comprises a rigid plate parallel to said downward facing surface, and a pad of resilient material fixed to said rigid plate between said rigid plate and said downward facing surface, thereby forming a horizontal slot between said resilient material and said downward facing surface.

13. Apparatus as in claim 11 further comprising solution agitation means in said reservoir.

14. Apparatus as in claim 11 wherein said aperture is profiled with a leading edge and a trailing edge running transverse to said direction of travel, said leading edge being substantially straight and not perpendicular to said direction of travel.

15. Apparatus as in claim 14 wherein said leading edge is oriented at 80 degrees to said direction of travel.

16. Apparatus as in claim 14 wherein said aperture is profiled as a parallelogram.

17. Apparatus as in claim 16 wherein said parallelogram has two sides which parallel said direction of travel.

* * * * *